(12) United States Patent
Anderson et al.

(10) Patent No.: US 6,420,360 B1
(45) Date of Patent: Jul. 16, 2002

(54) SULTAM AND SULTONE DERIVED OXAZOLIDINONES

(75) Inventors: David John Anderson, Kalamazoo; Jackson B. Hester, Jr., Galesburg, both of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/032,958

(22) Filed: Nov. 1, 2001

Related U.S. Application Data

(62) Division of application No. 09/699,709, filed on Oct. 30, 2000, now Pat. No. 6,348,459.
(60) Provisional application No. 60/163,537, filed on Nov. 4, 1999.

(51) Int. Cl.[7] .................. A61K 31/54; A61K 31/39; A61P 31/04; C07D 279/02; C07D 327/06
(52) U.S. Cl. ........................................ 514/222.2; 544/3
(58) Field of Search ............................ 514/222.2; 544/3

(56) References Cited

U.S. PATENT DOCUMENTS

| 4,709,026 A | 11/1987 | Guenther .................. 544/3 |
| 6,166,056 A | * 12/2000 | Thomas et al. .............. 514/376 |

FOREIGN PATENT DOCUMENTS

| WO | WO 97/09328 | 3/1997 |
| WO | WO 97/30995 | 8/1997 |
| WO | WO 98/54161 | 12/1998 |
| WO | WO 99/10342 | 3/1999 |
| WO | WO 99/29688 | 6/1999 |

OTHER PUBLICATIONS

DuPriest et al., Journal of Medicinal Chemistry. 1991 34, p. 3229.
Morris et al., Journal of Organic Chemistry 1991, 56, 3549–3556.
Zurenko et al., Oxazolidinone antibacterial agents: development of the clinical candidates eperezolid and linezolid Exp. Opin. Invest. Drugs 1997 6(2) 151–158.

* cited by examiner

Primary Examiner—Mukund J. Shah
Assistant Examiner—Venkataraman Balasubramanian
(74) Attorney, Agent, or Firm—Lucy X. Yang; Jonathan P. O'Brien

(57) ABSTRACT

The present invention provides a compound of formula I

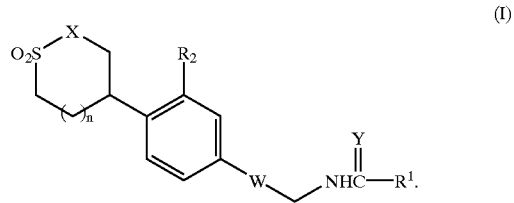

These compounds are useful as antibiotic agents.

5 Claims, No Drawings

SULTAM AND SULTONE DERIVED OXAZOLIDINONES

CROSS-REFERENCE TO RELATED APPLICATIONS

This application is a divisional application of U.S. patent application Ser. No. 09/699,709, now U.S. Pat. No. 6,348,459, which in turn claims the benefit of the following provisional application: U.S. Ser. No. 06/163,537, filed Nov. 4, 1999, which is incorporated herein by reference in its entirety.

BACKGROUND OF THE INVENTION

The present invention provides sultam and sultone derived oxazolidinones, and more specifically, provides compounds of formula (I) described herein below. These compounds are useful as antibiotic agents.

The oxazolidinone antibacterial agents are a novel synthetic class of antimicrobials with potent activity against a number of human and veterinary pathogens, including gram-positive aerobic bacteria such as multiply-resistant staphylococci and streptococci, gram-negative aerobic bacteria such as *H. influenzae* and *M. catarrhalis,* as well as anaerobic organisms such as bacteroides and clostridia species, acid-fast organisms such as *Mycobacterium tuberculosis* and *Mycobacterium avium.*

INFORMATION DISCLOSURE

International Publication No. WO 97/09328 discloses phenyloxazolidinones having a C—C bond to 4–8 membered heterocyclic rings useful as antimicrobial agents.

U.S. Pat. No. 4,709,026 discloses ketosultams useful as sensitizers or dyes.

J. Org. Chem. 1991, 56, 3549–3556 discloses vinyl sulfonyl esters and amides in the synthesis of substituted δ-sultams and δ-sultones.

SUMMARY OF THE INVENTION

The present invention provides a compound of formula I:

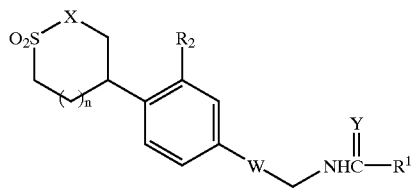

(I)

or a pharmaceutically acceptable salt thereof wherein

W is a structure i or ii;

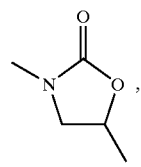

i

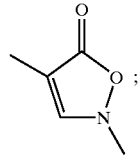

ii $R^1$ is
(a) H,
(b) $C_{1-8}$ alkyl, optionally substituted with one to three F, Cl, OH, OC(=O)$C_{1-4}$ alkyl, or O$C_{1-4}$ alkyl,
(c) $C_{3-6}$ cycloalkyl,
(d) amino,
(e) $C_{1-8}$ alkylamino,
(f) $C_{1-8}$ dialkylamino, or
(g) O$C_{1-8}$ alkyl;

$R^2$ is H or F;

X is O or N$R^3$;

$R^3$ is
(a) H,
(b) $C_{1-8}$ alkyl, optionally substituted with one to three F, Cl, OH, CN, NH$_2$, OC(=O)$C_{1-4}$ alkyl, or O$C_{1-4}$ alkyl,
(c) $C_{3-8}$ alkene, or
(d) C(=O)N$R^4R^5$;

$R^4$ and $R^5$ are independently
(a) H, or
(b) $C_{1-8}$ alkyl, optionally substituted with one to three F, Cl, OH, CN, or NH$_2$;

Y is O or S; and n is 0 or 1.

In another aspect, the present invention also provides:

a pharmaceutical composition comprising a compound of formula I, or a pharmaceutically acceptable salt thereof, and a pharmaceutically acceptable excipient (the composition preferably comprises an effective amount of the compound or salt), a method of treating or preventing microbial infections in a mammal including skin and eye infections, comprising administering to said mammal in need of such treatment, a compound of formula (I) or a pharmaceutically acceptable salt thereof, and a compound of formula (I) or a pharmaceutically acceptable salt thereof for use in medical treatment (e.g. the treatment or prevention of a microbial infection), and The invention also provides novel intermediates and processes disclosed herein that are useful for preparing compounds of formula I.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Specific and preferred values listed below for radicals, substituents, and ranges, are for illustration only; they do not exclude other defined values or other values within defined ranges for the radicals and substituents.

The following definitions are used, unless otherwise described.

Alkyl denotes both straight and branched groups; but reference to an individual radical such as "propyl" embraces only the straight chain radical, a branched chain isomer such as "isopropyl" being specifically referred to. Specifically, $C_{1-8}$ alkyl can be methyl, ethyl, propyl, isopropyl, butyl, iso-butyl, sec-butyl, pentyl, 3-pentyl, hexyl, heptyl, octyl and their isomeric forms thereof. Specifically, $C_{1-4}$ alkyl can be methyl, ethyl, propyl, isopropyl, butyl, iso-butyl, sec-butyl, and their isomeric forms thereof.

Alkene denotes both straight and branched groups having at least one double bond. Specifically, $C_{3-8}$ alkene can be allyl, butenyl, pentenyl, hexenyl, heptenyl, octenyl and their isomeric forms thereof.

$C_{3-6}$ cycloalkyl denotes a cycloalkyl having three to six carbon atoms. Specifically, $C_{3-6}$ cycloalkyl can be cyclopropyl, cyclobutyl, cyclopentyl, or cyclohexyl.

Mammal denotes human and other warm blooded animals.

Pharmaceutically acceptable salts denotes those salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, methanesulfonic acid salt and etc.

Compounds of the present invention may be in a form of pharmaceutically acceptable salts.

It is to be understood that the present invention encompasses any racemic, optically-active, polymorphic, tautomeric, or stereoisomeric form, or mixture thereof.

A specific value for $R^1$ is H.

A specific value for $R^1$ is $C_{1-8}$ alkyl, optionally substituted with one to three F, Cl, OH, OC(=O)$C_{1-4}$ alkyl, or $OC_{1-4}$ alkyl.

A specific value for $R^1$ is $C_{3-6}$ cycloalkyl.

A specific value for $R^1$ is amino, $C_{1-8}$ alkylamino, $C_{1-8}$ dialkylamino.

A specific value for $R^1$ is $OC_{1-8}$ alkyl.

A preferred value for $R^1$ is methyl.

A specific value for $R^2$ is F.

A specific value for X is O.

A specific value for X is $NR^3$; wherein $R^3$ is H.

A specific value for X is $NR^3$; wherein $R^3$ is $C_{1-8}$ alkyl, optionally substituted with one to three F, Cl, OH, CN, $NH_2$, OC(=O)$C_{1-4}$ alkyl, or $OC_{1-4}$ alkyl.

A specific value for X is $NR^3$; wherein $R^3$ is $C_{3-8}$ alkene.

A specific value for X is $NR^3$; wherein $R^3$ is C(=O)$NR^4R^5$; wherein $R^4$ and $R^5$ are independently H or $C_{1-8}$ alkyl, optionally substituted with one to three F, Cl, OH, CN, or $NH_2$;

A preferred value for X is O.

Another preferred value for X is NH.

Another preferred value for X is $NCH_3$.

A specific value for Y is O.

A specific value for Y is S.

A specific value for n is 0 or 1.

A preferred value for n is 1.

A preferred structure is structure I-A

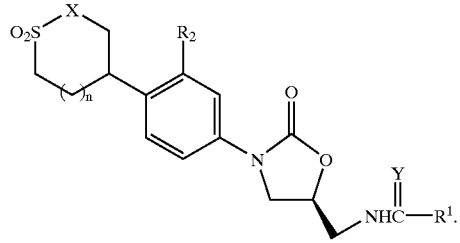

I-A

Examples of the present invention includes:

a) N-[[(5S)-3-[3-fluoro-4-[tetrahydro-1,1-dioxido-2-(2-propenyl)-2H-1,2-thiazin-4-yl]phenyl]-2-oxo-5-oxazolidinyl]methyl]acetamide, b) N-[[(5S)-3-[3-fluoro-4-(tetrahydro-1,1-dioxido-2H-1,2-thiazin-4-yl)phenyl]-2-oxo-5-oxazolidinyl]methyl] acetamide, c) N-[[(5S)-3-[3-fluoro-4-(tetrahydro-1,1-dioxido-2H-1,2-thiazin-4-yl)phenyl]-2-oxo-5-oxazolidinyl]methyl] ethanethioamide, d) N-[[(5S)-3-[-fluoro-4-(tetrahydro-2-methyl-1,1-dioxido-2H-1,2-thiazin-4-yl)phenyl]-2-oxo-5-oxazolidinyl] methyl]ethanethioamide, e) N-[[(5S)-3-[4-(2,2-dioxido-1,2-oxathian-5-yl)-3-fluorophenyl]-2-oxo-5-oxazolidinyl]methyl] ethanethioamide, f) N-[[(5S)-3-[4-(1,1-dioxido-4-isothiazolidinyl)-3-fluorophenyl]-2-oxo-5-oxazolidinyl]methyl] ethanethioamide, or g) N-[[(5S)-3-[3-fluoro-4-(tetrahydro-2-methyl-1,1-dioxido-2H-1,2-thiazin-4-yl)phenyl]-2-oxo-5-oxazolidinyl]methyl]acetamide.

The following Schemes describe the preparation of compounds of the present invention. All of the starting materials are commercially available or prepared by procedures described in these schemes or by procedures that would be well known to one of ordinary skill in organic chemistry. The variables used in the Schemes are as defined above or as in the claims.

The 6-membered ring sultams (n=1, X=$NR^3$, $R^3$ is the same as defined above) may be prepared as outlined in Scheme 1. Also see Morris et al., *J. Org. Chem.*, 1991, 56, 3549. Addition of aryl acetic acid ester 2 to vinyl sulfonamide 3 in the presence of base gives adduct 4. Removal of the protecting groups from 4 with trifluoroacetic acid gives 5. Ring closure of 5 with sodium hydride affords 6 which in turn may be reduced with sodium borohydride-trifluoroacetic acid to give sultam 7. The nitrogen atom of the sultam ring may be protected with an allyl group to give 8 and the nitro group of 8 subsequently reduced with sodium borohydride-cuprous bromide: dimethyl sulfide complex to give amine 9.

Amine 9 can be protected as a CBZ derivative 10 which in turn can be reacted with amido epoxide 11 in the presence of base to give oxazolidinone 12. Removal of the N-allyl group can be effected with palladium on carbon in the presence of boron trifluoride etherate in ethanol to give 13. Replacement of H with $R^3$ using methods known to those skilled in the art provides compound 14. Finally, thioamide 15 may be prepared by treating amide 14 with Lawesson's Reagent.

The 6-membered ring sultones (n=1, X=O) may be prepared analogously to the sultams and the syntheses are outlined in Scheme II. Addition of methyl arylacetate 2 to vinyl sulfonate in the presence of base affords adduct 16. Reduction of the ester of 16 with DIBAL gives alcohol 17 which may be cyclized to sultone 18 in the presence of sodium hydride. A similar sequence of steps to those outlined for the sultam in Scheme I, converts 18 to the sultone oxazolidinones 19.

The preparation of 5-membered ring sultam is outlined in Scheme III. Alkylation of methyl arylacetate 2 with bromomethylsulfonamide 20 gives the adduct 21, which in the presence of base may be cyclized to 22. A similar sequence of steps as outlined in Scheme 1 converts 22 to sultam oxazolidinones 23. See DuPriest at al., *J.Med Chem.* 1991, 34, 3229 and Morris et al., *J org. Chem.,* 1991, 56, 3549.

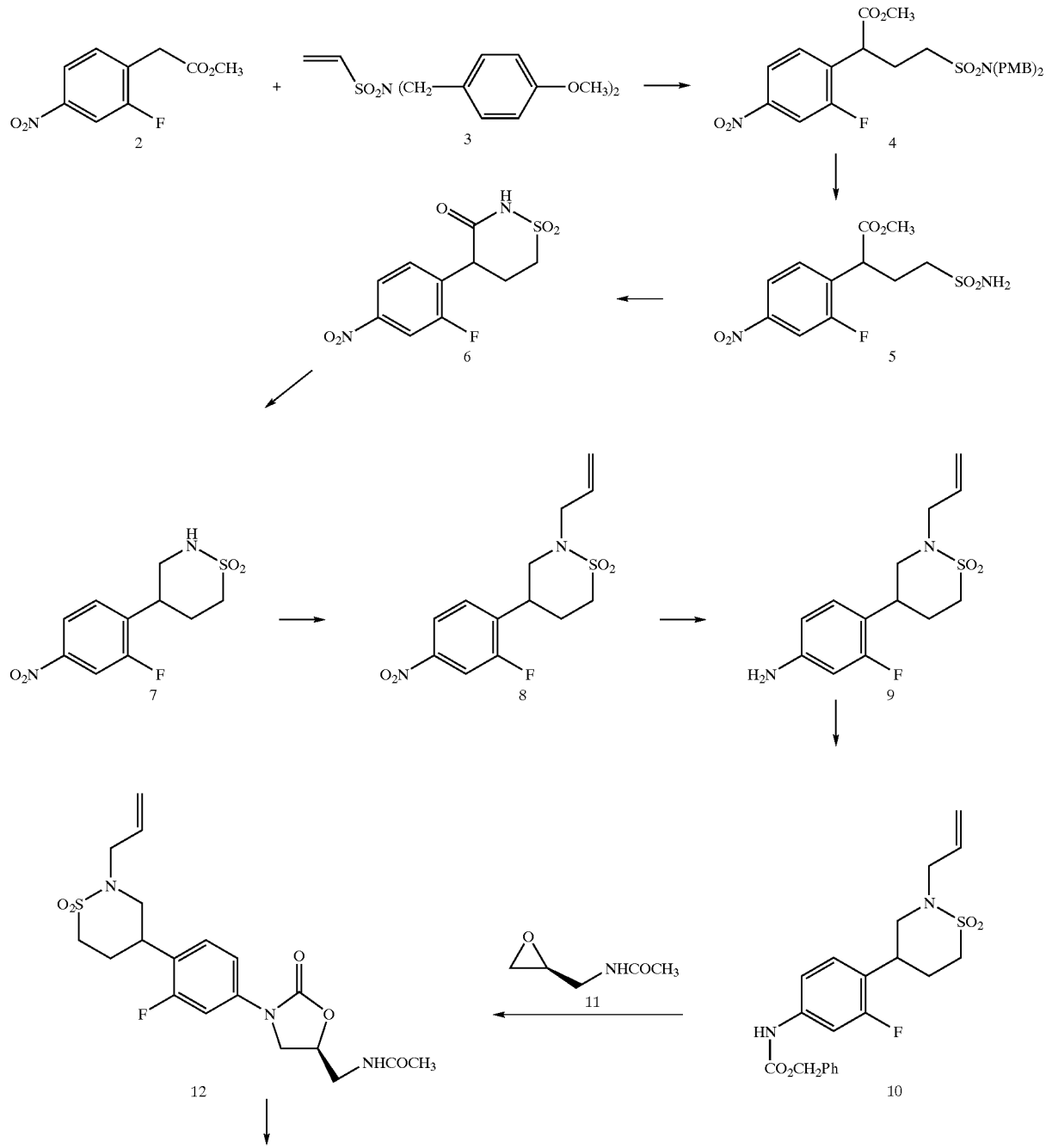

SCHEME I

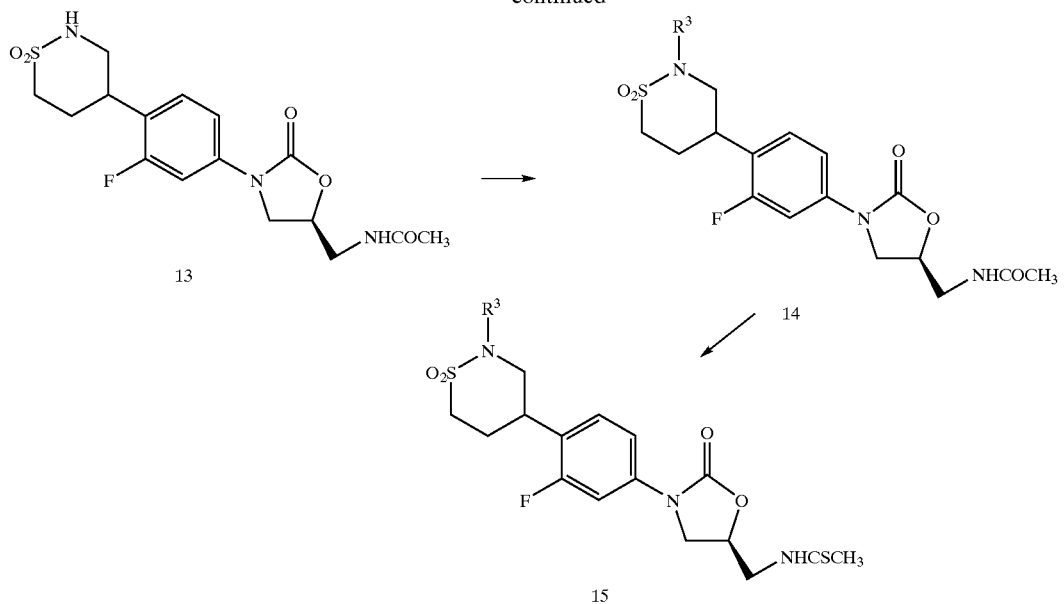
SCHEME II
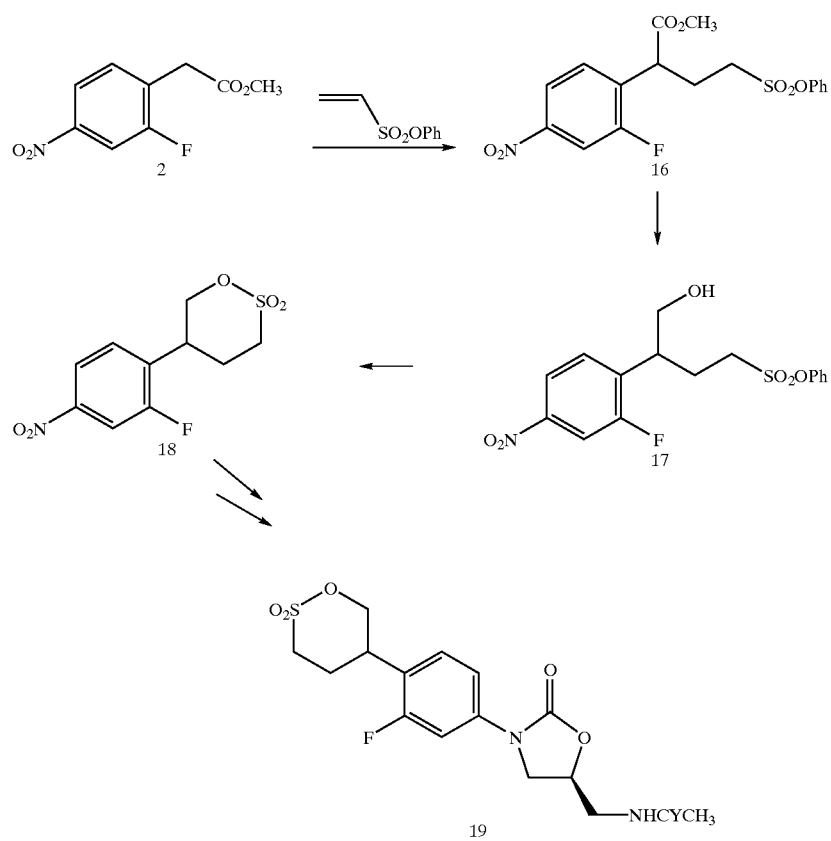

SCHEME III

-continued

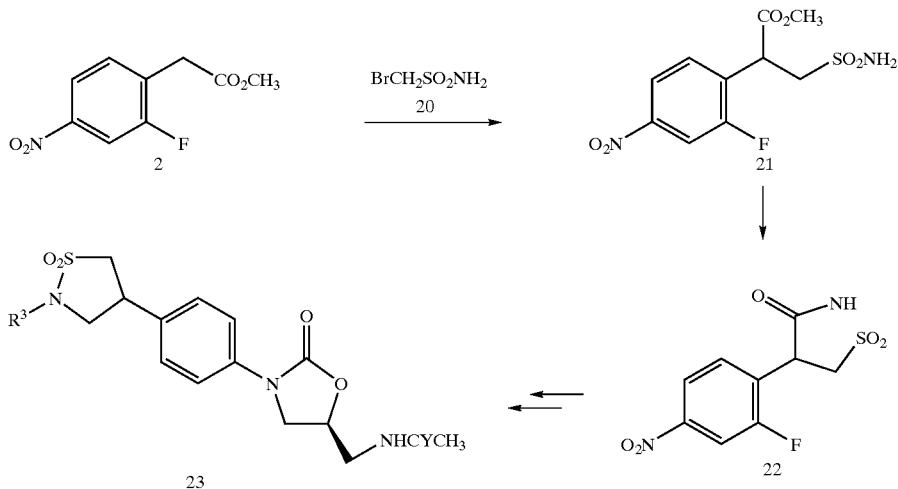

The compounds and their preparations of the present invention will be better understood in connection with the following examples, which are intended as an illustration of and not a limitation upon the scope of the invention.

EXAMPLES

Example 1

Preparation of N-[[(5S)-3-[3-fluoro-4-[tetrahydro-1,1-dioxido-2-(2-propenyl)-2H-1,2-thiazin-4-yl]phenyl]-2-oxo-5-oxazolidinyl]methyl]acetamide

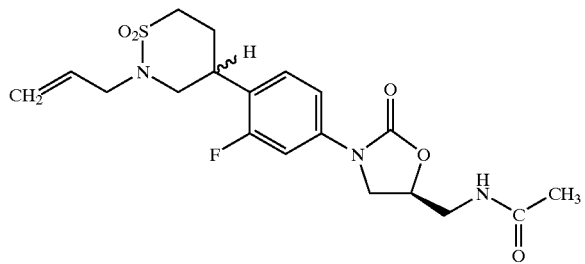

Step 1

Preparation of methyl .alpha.-[2-[[bis[(4-methoxyphenyl)methyl]amino]sulfonyl]ethyl]-2-fluoro-4-nitrobenzeneacetate Methyl 2-(2-fluoro-4-nitrophenyl)acetate (25.0 g, 117.4 mmol), vinyl sulfonamide (35.0 g, 100.9 mmol), anhydrous potassium carbonate (10.0 g, 72.5 mmol) and 18-crown-6 (2.64 g, 10.0 mmol) are heated under reflux in toluene (250 ml) for 3 hr. After cooling, ethyl acetate (500 ml) and water (300 ml) are added. The organic layer is washed with brine (200 ml), dried over MgSO$_4$, filtered and evaporated. The resultant oil is chromatographed over silica gel (1 kg) eluting with 25–50% ethyl acetate-hexane. The title compound is obtained as white crystals (45.8 g, 81%) mp 79°.

Step 2

Preparation of methyl .alpha.-[2-(aminosulfonyl)ethyl]-2-fluoro-4-nitrobenzeneacetate Methyl .alpha.-[2-[[bis[(4-methoxyphenyl)methyl]amino]sulfonyl]ethyl]-2-fluoro-4-nitrobenzeneacetate (41.6 g, 74.3 mmol) is dissolved in methylene chloride (200 ml) and trifluoroacetic acid (50 ml). The solution is stirred for 2 days then the solvents evaporated. The residue is dissolved in ethyl acetate (750 ml) and washed with sodium bicarbonate solution (200 ml) and brine (100 ml). After drying (MgSO$_4$), filtration and evaporation the title compound is obtained as a solid (20.5 g, 86%) mp 99–101°.

Step 3

Preparation of 4-(2-Fluoro-4-nitrophenyl)dihydro-2H-1,2-thiazin-3(4H)-one 1,1-dioxide A 60% sodium hydride oil dispersion (520 mg, 13.0 mmol) is washed with hexane (3×5 ml) then dry tetrahydrofuran (30 ml) added. To this stirred ice cooled mixture is added a solution of methyl .alpha.-[2-(aminosulfonyl)ethyl]-2-fluoro-4-nitrobenzeneacetate (3.20 g, 10.0 mmol) in dry tetrahydrofuran (30 ml). After stirring for 3 hr, additional sodium hydride (300 mg, 7.5 mmol) is added. Methanol (5 ml) is added after an additional 20 hr and the reaction evaporated to dryness. The residue is partitioned between 5% methanol-chloroform (150 ml) and 1N.HCl (50 ml), and the brown solid filtered. This solid is chromatographed over silica gel (150 g) eluting with 50% acetone-hexane. Recrystallization from acetone-hexane gives the title compound as solid. mp 218–219°.

Step 4

Preparation of 4-(2-Fluoro-4-nitrophenyl)tetrahydro-2H-1,2-thiazine 1,1-dioxide 4-(2-Fluoro-4-nitrophenyl)dihydro-2H-1,2-thiazin-3(4H)-one 1,1-dioxide (2.43 g, 8.44 mmol) and sodium borohydride (3.83 g, 101.3 mmol) are placed under nitrogen and dry THF (70 ml) added. To the ice cooled suspension is added trifluoroacetic acid (7.8 ml, 101.3 mmol) over 5 min. After stirring for 16 hr additional trifluoroacetic acid (20.0 ml, 260 mmol) is added followed by methanol (20 ml). The solution is evaporated and the residue dissolved in ethyl acetate (150 ml) and washed with sodium bicarbonate solution (3×100 ml) and brine (50 ml). Evaporation gives a yellow gum which is chromatographed over silica gel (90 g) eluting with 1–3% methanol-chloroform. The title compound is obtained as a gum (1.99 g, 86%): Calcd for

11

C₁₀H₁₁FN₂O₄S: C, 43.79; H, 4.04; N, 10.21. Found: C, 43.72; H, 4.07; N, 10.11.

Step 5

Preparation of 4-(2-fluoro-4-nitrophenyl)tetrahydro-2-(2-propenyl)-2H-1,2-thiazine 1,1-dioxide Anhydrous potassium carbonate (3.6 g, 26.1 mmol) is added to a solution of of 4-(2-fluoro-4-nitrophenyl)tetrahydro-2H-1,2-thiazine 1,1-dioxide (1.795 g, 6.54 mmol) and allyl bromide (2.0 ml, 23.1 mmol) in dry acetonitrile (25 ml). The mixture is heated to reflux for 5 min then cooled. After filtration and evaporation the residue is chromatographed over silica gel (150 g) eluting with 0–1% methanol-chloroform. The title compound is obtained as flakes (1.70 g, 83%) mp 121°.

Step 6

Preparation of 3-fluoro-4-[tetrahydro-1,1-dioxido-2-(2-propenyl)-2H-1,2-thiazin-4-yl]benzenamine 4-(2-Fluoro-4-nitrophenyl)tetrahydro-2-(2-propenyl)-2H-1,2-thiazine 1,1-dioxide (1.303 g, 4.15 mmol) and cuprous bromide: dimethyl sulfide complex (0.855 g, 4.15 mmol) are stirred at ice temperature in dry THF (30 ml). Sodium borohydride (1.25 g, 33.07 mmol) is added and the mixture stirred for 20 min. Methanol (10 ml) is carefully added over 30 min followed by ammonium chloride solution (50 ml). The mixture is extracted with methylene chloride (2×100 ml), washed with water (50 ml) and brine (50 ml), dried (MgSO₄) and evaporated to yield the product as a cream solid (1.178 g, 100%) mp 96°.

Step 7

Preparation of phenylmethyl [3-fluoro-4-[tetrahydro-1,1-dioxido-2-(2-propenyl)-2H-1,2-thiazin-4-yl]phenyl]carbamate 3-fluoro-4-[tetrahydro-1,1-dioxido-2-(2-propenyl)-2H-1,2-thiazin-4-yl]benzenamine (1.154 g, 4.06 mmol) is dissolved in THF (15 ml) to which is added benzyl chloroformate (765 mg, 4.48 mmol) followed by a solution of sodium bicarbonate (700 mg, 8.33 mmol) in water (10 ml). After stirring for 2 hr most of the THF is evaporated and the residue is extracted with ethyl acetate (100 ml). After washing with water (25 ml) and brine, the solution is dried (MgSO₄) and evaporated to afford the title compound as white crystals (1.70 g, 100%) mp 138–140°.

Step 8

Preparation of N-[[(5S)-3-[3-fluoro-4-[tetrahydro-1,1-dioxido-2-(2-propenyl)-2H-1,2-thiazin-4-yl]phenyl]-2-oxo-5-oxazolidinyl]methyl]acetamide Phenylmethyl [3-fluoro-4-[tetrahydro-1,1-dioxido-2-(2-propenyl)-2H-1,2-thiazin-4-yl]phenyl]carbamate (1.70 g, 4.07 mmol) is dissolved in dry THF (18 ml) under nitrogen and cooled to −78°. A 1.6 M solution of n-butyl lithium (2.7 ml, 4.32 mmol) in hexane is added and stirred for 1 hr. A solution of N-[(2S)oxiranylmethyl]acetamide 11 (960 mg, 8.35 mmol) in dry THF (6.5 ml) is added and the stirred mixture allowed to come to 25° overnight. Solvent is evaporated and the residue partitioned between chloroform (100 ml) and ammonium chloride solution (50 ml). The organic layer is washed with brine (40 ml), dried (MgSO₄) and evaporated. The residue is chromatographed over silica gel (150 g) eluting with 2–4% methanol-chloroform to afford the oxazolidinone as a white foam (1.275 g, 73%). HRMS (FAB) calcd for m+H=426.1499: Found; 426.1506.

12

Example 2

Preparation of N-[[(5S)-3-[3-fluoro-4-(tetrahydro-1,1-dioxido-2H-1,2-thiazin-4-yl)phenyl]-2-oxo-5-oxazolidinyl]methyl]acetamide

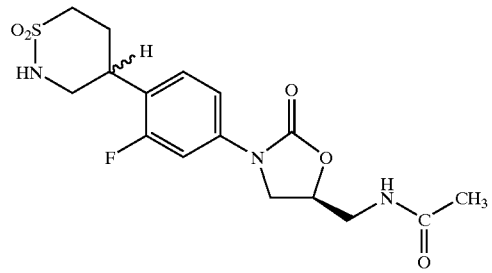

N-[[(5S)-3-[3-Fluoro-4-[tetrahydro-1,1-dioxido-2-(2-propenyl)-2H-1,2-thiazin-4-yl]phenyl]-2-oxo-5-oxazolidinyl]methyl]acetamide (350 mg, 0.82 mmol), 10% palladium on carbon (500 mg), boron trifluoride etherate (179 mg, 1.26 mmol) and absolute ethanol (8 ml) are heated under reflux for 5 hr. Upon cooling the suspension is filtered and evaporated. Chromatography over silica gel (55 g) eluting with 2–6% methanol-chloroform affords the title compound as a foam (186 mg, 59%). HRMS(FAB): calcd for m+H=386.1186; Found: 386.1194.

Example 3

Preparation of N-[[(5S)-3-[3-fluoro-4-(tetrahydro-1,1-dioxido-2H-1,2-thiazin-4-yl)phenyl]-2-oxo-5-oxazolidinyl]methyl]ethanethioamide

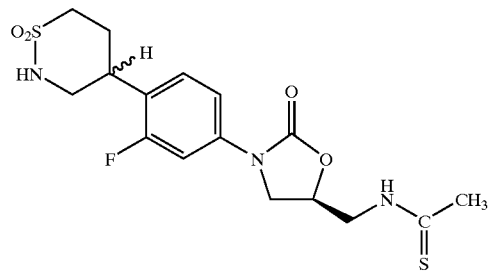

N-[[(5S)-3-[3-Fluoro-4-(tetrahydro-1,1-dioxido-2H-1,2-thiazin-4-yl)phenyl]-2-oxo-5-oxazolidinyl]methyl]acetamide (180 mg, 0.47 mmol), Lawesson's Reagent (310 mg, 0.77 mmol) and dioxane (10 ml) are heated under reflux for 1 hr. After cooling, the solvent is evaporated and the residue chromatographed over silica gel (40 g) eluting with 2–4% methanol-chloroform gives the title compound as a foam (173 mg, 92%). HRMS(FAB): calcd for m+H= 402.0957; Found: 402.0954.

Example 4

Preparation of N-[[(5S)-3-[3-fluoro-4-(tetrahydro-2-methyl-1.1-dioxido-2H-1,2-thiazin-4-yl)phenyl]-2-oxo-5-oxazolidinyl]methyl]acetamide

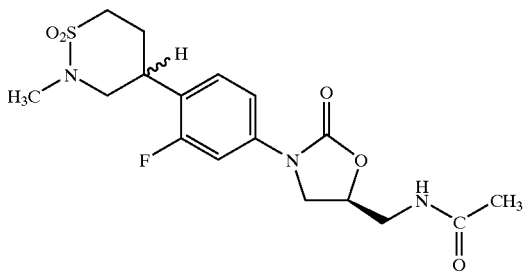

N-[[(5S)-3-[3-fluoro-4-(tetrahydro-1,1-dioxido-2H-1,2-thiazin-4-yl)phenyl]-2-oxo-5-oxazolidinyl]methyl] acetamide (200 mg, 0.52 mmol), powdered potassium carbonate (85 mg, 0.62 mmol) and methyl iodide (88 mg, 0.62 mmol) were stirred under nitrogen in dry DMF (1 mL) for 24 hours. After evaporation of the solvent, the residue is partitioned between chloroform (65 mL) and water (15 mL). The chloroform is dried (MgSO$_4$), filtered and evaporated. The residue is chromatographed over silica gel, eluting with 2–6% methanol-chloroform. The product is obtained as a white foam (156 mg, 75%). HRMS (FAB) calc'd for M+H= 400.1342; Found: 400.1343.

Example 5

Preparation of N-[[(5S)-3-[3-fluoro-4-(tetrahydro-2-methyl-1,1-dioxido-2H-1,2-thiazin-4-yl)phenyl]-2-oxo-5-oxazolidinyl]methyl]ethanethioamide

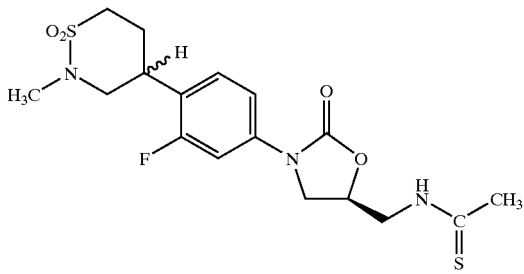

N-[[(5S)-3-[3-fluoro-4-(tetrahydro-2-methyl-1,1-dioxido-2H-1,2-thiazin4-yl)phenyl]-2-oxo-5-oxazolidinyl] methyl]acetamide (100 mg, 0.25 mmol) and Lawesson's Reagent (122 mg, 0.30 mmol) were dissolved in dioxane (10 mL) under nitrogen. The reaction is heated to 100° C. for 20 minutes then cooled to ambient and evaporated. The residue is partitioned between ethyl acetate (150 mL) and water (50 mL). The organic phase is washed 3 times with water (50 mL) and brine (50 mL), then dried over MgSO$_4$, filtered and evaporated to a nearly colorless glass. The product is purified by radial chromatography over silica gel, eluting with 0–10% methanol-methylene chloride to give a white solid foam (89 mg, 85%). MP=95–98° C., decomposes.

The pharmaceutical compositions of this invention may be prepared by combining the compounds of formula I of this invention with a solid or liquid pharmaceutically acceptable carrier and, optionally, with pharmaceutically acceptable adjuvants and excipient employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combatting, bacterial infections in human and other warm blooded animals, the compounds or pharmaceutical compositions thereof will be administered orally, topically, transdermally, and/or parenterally at a dosage to obtain and maintain a concentration an amount, or blood-level of active component in the mammals undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are also administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formulas I according to this invention are advantageously administered orally in solid and liquid dosage forms.

We claim:

1. A method for treating microbial infections in a mammal which comprises administering to said mammal in need thereof an effective amount of a compound of Formula I.

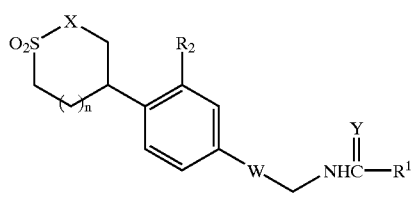

(I)

or a pharmaceutically acceptable salt thereof wherein

W is a structure i or ii

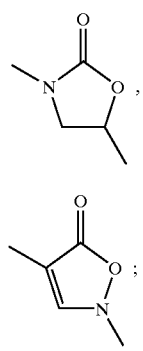

$R^1$ is
(a) H,
(b) $C_{1-8}$ alkyl, optionally substituted with one to three F, Cl, OH, OC(=O)$C_{1-4}$ alkyl, or O$C_{1-4}$ alkyl,
(c) $C_{3-6}$ cycloalkyl,
(d) amino,
(e) $C_{1-8}$ alkylamino,
(f) $C_{1-8}$ dialkylamino, or
(g) O$C_{1-8}$ alkyl;

$R^2$ is H or F;

X is O or N$R^3$;

$R^3$ is
(a) H,
(b) $C_{1-8}$ alkyl, optionally substituted with one to three F, Cl, OH, CN, NH$_2$, OC(=O)$C_{1-4}$ alkyl, or O$C_{1-4}$ alkyl,
(c) $C_{3-8}$ alkene, or
(d) C(=O)N$R^4R^5$;

$R^4$ and $R^5$ are independently
(a) H, or
(b) $C_{1-8}$ alkyl, optionally substituted with one to three F, Cl, OH, CN, or NH$_2$;

Y is O or S; and n is 0 or 1.

2. The method of claim 1 wherein said compound of formula I is administered orally, parenterally, transdermally, or topically in a pharmaceutical composition.

3. The method of claim 1 wherein said compound is administered in an amount of from about 0.1 to about 100 mg/kg of body weight/day.

4. A method for treating microbial infections of claim 1 wherein the infection is skin infection.

5. A method for treating microbial infections of claim 1 wherein the infection is eye infection.

* * * * *